United States Patent [19]

Larrick et al.

[11] Patent Number: 5,001,065
[45] Date of Patent: Mar. 19, 1991

[54] HUMAN CELL LINE AND TRIOMAS, ANTIBODIES, AND TRANSFORMANTS DERIVED THEREFROM

[75] Inventors: James W. Larrick, Woodside; George Senyk, San Francisco, both of Calif.

[73] Assignee: Cetus Corporation, Emeryville, Calif.

[21] Appl. No.: 54,441

[22] Filed: May 27, 1987

[51] Int. Cl.$^5$ .......................... C12N 5/24; C12N 15/07
[52] U.S. Cl. ........................... 435/240.26; 435/240.27; 435/172.2; 435/948; 935/89; 935/95; 935/99; 935/100; 935/93
[58] Field of Search ................. 435/68, 172.2, 240.26, 435/240.27, 948; 935/52, 56, 93, 100, 106

[56] References Cited

U.S. PATENT DOCUMENTS

| | | | |
|---|---|---|---|
| 4,434,230 | 1/1984 | Ritts, Jr. | 435/240.27 |
| 4,529,694 | 7/1985 | Lazarus et al. | 435/68 |
| 4,624,921 | 11/1986 | Larrick et al. | 435/172.2 |
| 4,634,664 | 1/1987 | Oestberg | 435/68 |
| 4,693,975 | 9/1987 | Kozbor et al. | 435/935 |

FOREIGN PATENT DOCUMENTS

| | | | |
|---|---|---|---|
| 0044722 | 1/1982 | European Pat. Off. | 435/172.2 |
| 0148644 | 7/1985 | European Pat. Off. | 435/68 |
| 0174204 | 12/1986 | European Pat. Off. | 435/240.27 |

OTHER PUBLICATIONS

Kozbor et al., Journal of Immunology 133(6), pp. 3001–3005 (1984).
Potter et al., Proc. Natl. Acad. Sci 81, pp. 7161–7165 (1984).
Kozbor et al., Proc. Natl. Acad. Sci. U.S.A., 79:6651–6655 (1982).
Kozbor et al., Human Hybridomas and Monoclonal Antibodies, Engleman et al., eds. (Plenum Press, 1985) pp. 21–36.
O'Hare et al., Protides of the Biological Fluids, Proceedings of the 13th Colloquium, 1982, H. Peeters, ed. (Oxford: Pergamon Press, 1983) pp. 265–268.
Pickering et al., J. Immunol., 129(1), 406–412 (1982).
Oestberg et al., Hybridoma, 2(4), 361–367 (1983).

Primary Examiner—Elizabeth C. Weimar
Assistant Examiner—Gail Poulos
Attorney, Agent, or Firm—Gregory J. Giotta; Janet E. Hasak; Albert P. Halluin

[57] ABSTRACT

A stable, continuous human cell line or progeny thereof is produced that is resistant to 6-thioguanine and ouabain, secretes less than 40 ng/ml of endogenous IgM antibodies, and grows with a doubling time of about 18 hours. The cell line, which preferably is adapted to serum-free medium, may be used as a fusion partner with an antibody-producing cell line so as to generate antibodies. In addition, it may be electroporated with a vector containing a gene of interest to produce a transformed cell line which generates a protein encoded by the gene, such as an IgG or IgM antibody.

5 Claims, No Drawings

HUMAN CELL LINE AND TRIOMAS, ANTIBODIES, AND TRANSFORMANTS DERIVED THEREFROM

BACKGROUND OF THE INVENTION

This invention relates to the fields of somatic cell hybridization, molecular biology, and immunochemistry. More particularly, it concerns a stable human cell line that is a low secretor of IgM and that can be used to prepare human×human×human triomas, human monoclonal antibodies, and transformants that can be used to express proteins of interest.

Kohler and Milstein, Nature (1975) 256:495–497, pioneered the use of somatic cell hybridization to make continuous hybridomas that produce monoclonal antibodies. Their work used plasmacytomas and lymphocytes of murine origin. Subsequent investigators have applied the techniques of Kohler and Milstein to human cells. Croce et al., Nature (London) (1980) 288:488 and Olsson and Kaplan, Proc. Nat. Acad. Sci. (USA) (1980) 77:5429.

The production of human monoclonal antibodies having a specificity and reproducibility similar to that of mouse monoclonal antibodies has been attempted using various methods. Such methods include, for example, transforming normal human lymphocytes with Epstein-Barr virus (EBV), culturing human B-lymphocytes with antigen, human serum and helper signal producing agents, fusing normal human lymphocytes to human myeloma cells, fusing normal human lymphocytes to an EBV-transformed human lymphoblastoid B-cell line, and fusing human lymphocytes to mouse myeloma or human/rodent heteromyeloma.

Transforming normal human lymphocytes with EBV, such as described in U.S. Pat. No. 4,464,465 and Steinitz, M., Nature (1977) 269:420–422, is cumbersome and therefore not commercially practical. Culturing human B-lymphocytes with antigen, serum and helper signal producing agents, as described in U.S. Pat. No. 4,444,887, requires a relatively complex procedure. Fusing normal human lymphocytes with human myeloma cells, as described by EP No. 44,722 and Cote et al., Proc. Natl. Acad. Sci. USA (1983) 80:2026–2030, is also not practicable due to the limited number of suitable human myeloma cell lines available. Olsson and Kaplan, Proc. Natl. Acad. Sci. USA (1980) 77:5429–5431 describes fusion of a mutant human myeloma cell line of U-266 with lymphoid cells from patients' spleens. Fusing normal human lymphocytes to an EBV-transformed human lymphoblastoid B-cell line suffers in that the capacity of the transformed lines to produce and secrete antibodies typically is such lower than that of myelomas. Examples of such procedures are described further below. Fusing human lymphocytes to mouse or human/rodent myeloma, such as described by U.S. Pat. Nos. 4,634,666 and 4,574,116 and by Kozbor et al., Hybridoma, (1982) 1:323–328, may result in an inherent genetic instability. U.S. Pat. No. 4,634,664 and Ostberg et al., Hybridoma, (1983) 2:361–367 disclose a hybridoma cell line comprising an immortalizing cell fused to a cell producing a predetermined human antibody, the immortalizing cell comprising a xenogeneic hybridoma cell fused from an immortalizing cell and a non-transformed partner cell, the antibody-producing cell being genetically compatible with the non-transformed partner cell. Bron et al., Proc. Natl. Acad. Sci. (1984) 81:3214–3217 describes fusion of an EBV-transformed human B-cell line with a mouse-human heteromyeloma.

Several references describe use of EBV-transformed human B lymphoblastoid cells in producing specific human antibodies. For example, Steinwitz et al., Nature (1977) 269:420 and Luzzanti et al., Nature (1977) 269:419 describe in vitro production of specific human antibodies from such transformed cells. While the EBV transformation allows these cells to be grown continuously, the cells typically lose their ability to secrete Ig in a short period of time.

Several recent references describe using EBV-transformed human lymphoblastoid cell lines as parental tumor partners in fusions with Ig-producing human lymphocytes. European Application No. 82301103.6 published Oct. 13, 1982 describes such a line designated WI-L2-729 HF$_2$. This line is reported to be a hypoxanthine phosphoribosyl transferase (HPRT)-deficient variant of the WI-L2 line (Levy, J. A. et al., Cancer (1968) 22:517). It is characterized as being nonsecreting, sIgM$_K$+, cyIgM$_K$+, and able to grow in serum-free media. Chiorazzi, N. et al., J. Exp. Med. (1982) 156:930–935 describes another EBV-transformed human lymphoblastoid cell line derived from the WI-L2 line. This other line, designated H35.1.1, appears to have different characteristics from the WI-L2-729 HF$_2$ line. Handley, H. H. et al., Proceedings of the 15th International Leucocyte Culture Conference, Asilomar (1982), p. 267, describes an intermediate parent of the WI-L2-729 HF$_2$ line, designated UC729-6. UC729-6 is reported to have characteristics common to WI-L2-729 HF$_2$ and was used as a fusion partner in making Ig-producing human×human hybridomas. U.S. Pat. No. 4,451,570 describes preparation of human monoclonal antibodies using a WI-L2 derivative that expresses IgM as the fusion partner. U.S. Pat. No. 4,624,921 discloses a subvariant of the EBV-transformed WI-L2 line, called LTR228, that fuses efficiently with human cells, and copending U.S. Ser. No. 604,069 filed Apr. 26, 1984 discloses fusing LTR228 with a human lymphocyte to produce anti-blood group substance-A antibodies.

Kozbor et al., Proc. Natl. Acad. Sci. USA (1982) 79:6651–6655 describes using an EBV-transformed Ig-producing human lymphocyte as a parental partner in fusion with a 6-thioguanine resistant human lymphoblastoid B-cell line mutagenized and selected for ouabain resistance.

Copending U.S. application Ser. No. 727,821 filed Apr. 26, 1985 and Teng et al., Proc. Natl. Acad. Sci. (USA) (1983) 80:7308–7312 disclose mouse×human fusion partner cell lines that can be fused with an antibody-producing human cell line to generate human monoclonal antibodies.

U.S. Pat. No. 4,529,694 discloses fusing human lymphocytes with a human fusion partner that is prepared by fusing human lymphocytes with human myeloma cells. U.S. Pat. No. 4,434,230 discloses hybridomas of human B-lymphocytes and a human non-secretory plasmacytoid continuous cell line. Pickering et al., J. Immunol. (1982) 129:406–412 discloses a human myeloma cell line that does not express immunoglobulin but yields a high frequency of antibody-secreting hybridomas. Kozbor et al. Human Hybridomas and Monoclonal Antibodies, Englemen et al. ed. (Plenum Press, New York, 1985), P. 21–36 disclose fusion partners for producing human monoclonal antibodies including human lymphoblastoid cell lines and non-Ig-secreting partners (p.32). O'Hare et al., *Protides of the Biological Fluids*, H. Peeters, ed. (Oxford: Pergamon Press, 1983), p.265-268 discloses a new human hybridoma system and alternatives regarding myeloma/lymphoblastoid lines and U-266.

There remains a need in the art for a stable, continuous human cell line that is easily electroporated with DNA for mammalian cell expression, grows rapidly, and secretes a minimal amount of IgM, but when fused to an antibody-producing cell line, secretes adequate amounts of immunoglobulin, including IgG.

SUMMARY OF THE INVENTION

Accordingly, the present invention provides a stable, continuous human cell line comprising a human immortalizing cell fused to an Epstein-Barr-virus-transformed human lymphoblastoid B cell line, said stable cell line being characterized by its resistance to 6-thioguanine and ouabain, its secretion of less than 40 ng/ml of IgM antibodies, and its growth with a doubling time of about 18 hours, or progeny of said cell line.

Preferably, the cell line is one that is adapted to serum-free medium, and most preferably is deposited as ATCC No. HB9320.

In another aspect, the present invention relates to a method for preparing such a cell line comprising:

(a) fusing human immortalizing cells with an Epstein-Barr-virus-transformed human lymphoblastoid B cell line in a fusion medium containing a fusogen;

(b) separating the cells from the fusion medium;

(c) incubating the cells in a nutrient medium for a sufficient time to expand the number of viable cells;

(d) growing the expanded cells in a medium and selecting those cells that are 6-thioguanine and ouabain resistant; and (e) selecting the cell lines for secretion of less than 40 ng/ml of IgM antibodies.

In a third aspect, the present invention relates to a monoclonal antibody-producing human×human×human trioma of:

(a) a stable, continuous human cell line comprising a human immortalizing cell fused to an Epstein-Barr-virus-transformed human lymphoblastoid B cell line, said stable cell line being characterized by its resistance to 6-thioguanine and ouabain, its secretion of less than 40 ng/ml of IgM antibodies, and its growth with a doubling time of about 18 hours, or progeny of said cell line; and (b) an antibody-producing human cell.

In a fourth aspect, the present invention provides a method of producing a human monoclonal antibody to a defined antigen comprising:

(a) growing the above-described trioma in a growth medium; and (b) isolating human monoclonal antibody from the growth medium.

In a fifth aspect, the present invention relates to a human monoclonal antibody produced by the above method.

In addition, the invention relates to a method of transforming the cell line herein comprising electroporating the cell line with a vector containing a gene encoding a protein of interest and regulatory DNA sequences for expressing the protein, as well as the transformed cell line so prepared.

Finally, the invention relates to a method for producing a protein comprising electroporating the cell line herein with a vector containing a gene encoding the protein and regulatory DNA sequences for expressing the protein, growing the cell line, and inducing the cell line to express the protein. In addition, the protein so produced is encompassed by the invention.

The cell line herein has the advantages that it fuses with high frequency to form hybrids that stably produce human IgG with low secretion of IgM. In addition, the cell line is able to be electroporated easily and may be useful for mammalian gene expression using EBV-based or other expression vectors.

DESCRIPTION OF THE PREFERRED EMBODIMENTS

As used herein, the term "cell line" refers to individual cells, harvested cells, and cultures containing cells, so long as they are derived from cells of the cell line referred to.

As used herein with respect to the described cell lines, the term "progeny" is intended to include all derivatives, issue, and offspring of cells of the described line regardless of generation or karyotypic identity. In this regard, it is well known that karyotypic changes may be induced or occur spontaneously, depending on the conditions under which the cells are maintained. In the case of the fusion partner herein, progeny that possess the fusability, 6-thioguanine and ouabain resistance, and growth characteristics of the fusion partner are preferred.

As used herein with respect to the parent cell line, the term "immortalizing cell" refers to a non-EBV-transformed neoplastic lymphoid cell, such as a myeloma or lymphoma.

As used herein with respect to the administration of antibody to patients, the term "treat" and conjugates thereof refer to therapy and/or prophylaxis.

As used herein, the term "monoclonal antibody" refers to an antibody selected from antibodies where the population is substantially homogeneous, i.e., the individuals of the antibody population are identical except for naturally occurring mutations.

As used herein with respect to characterizing the claimed hybrid cell lines, the terms "continuous" and "stable" mean that the lines remain viable over a prolonged time, typically at least about six months, and the antibody-producing lines maintain the ability to produce the specified monoclonal antibody through at least about 25 passages.

The human cell line herein that may be used as a fusion partner comprises the fusion product of a human immortalizing cell and an EBV-transformed human lymphoblastoid B cell line.

An example of an EBV-transformed human lymphoblastoid B cell line useful herein, and one that is in fact preferred, is the LTR228 cell line described in U.S. Pat. No. 4,634,921, the disclosure of which is incorporated herein by reference. LTR228 is a subvariant of the WI-L2 line and was derived from a mycoplasma-contaminated generic WI-L2 parent by cloning the parent in soft agar, decontaminating the parent line, and culturing it in Iscove's medium containing 20 µg/ml 6-thioguanine (6-TG). LTR228 was selected from among the 6-TG resistant clones on the basis of its ability to fuse efficiently with normal B lymphocytes. LTR228 was deposited with the American Type Culture Collection (ATCC), 12301 Parklawn Drive, Rockville, Md., U.S.A. on Feb. 14, 1984 and has ATCC No. HB8502. Other suitable human lymphoblastoid lines may be employed, such as P3-J described by Kamei, *Experientia*

(1968) 25:410–411 or GM1500 6TG A-11 described by Kozbor et al., *Proc. Natl. Acad. Sci. USA* (1982) 79:6651–6655, if they produce the fusion partner with the characteristics described herein.

An example of a human immortalizing cell that may be employed in the production of the fusion partner herein, and preferred herein, is a human myeloma designated U266B1. This cell line was first described by Dr. K. Nilsson et al., *Clin. Exp. Immunol.* (1970) 7:477–489, the disclosure of which is incorporated herein by reference. This cell line, deposited as ATCC TIB196, is a stable human myeloma secreting IgEλ that is HAT medium sensitive and unable to metabolize hypoxanthine. Immunological studies indicate that the U266 cell line was derived from the same clone of myeloma cells that grew in vivo, because the Ig produced in vitro is the same as that produced in vivo.

Another suitable human myeloma cell line herein is the HAT-sensitive cell line, SKO-007, derived from U266, assigned ATCC No. CRL 8033, and described in European Patent Publication No. 044,722, the disclosure of which is incorporated herein by reference.

Additional human myeloma cell lines that may be employed include, e.g., the GM1500 B cell line described by Croce et al., *Nature* (1980) 288:488, the RPMI8226 myeloma line described by Clark et al., *J. Supramol. Struct. Cell. Biochem.* (1981) Suppl. 5:100a, the variant of RPMI8226 that is 8-azaguanine resistant that does not secrete intact immunoglobulin molecules, described by Pickering et al., *J. Immunol.* (1982) 129:406–412, and the derivative of ARH-77 described by Edwards et al., *Eur. J. Immunol.* (1982) 12:641–648, the disclosures of all of which articles are incorporated by reference.

Before fusion, the lymphoblastoid cell line, such as LTR228, may be made resistant to ouabain, if it is not already resistant. Ouabain resistance may be effected by culturing the lymphoblastoid cells in media containing increasing concentrations of ouabain, as described in more detail hereinbelow.

The immortalizing cell line and lymphoblastoid cell line are fused by contacting the parent cells in a fusogen-containing medium under conditions that promote formation of viable hybrids. The fusion medium typically comprises a balanced salt solution such as Hank's balanced salt solution containing polyethylene glycol (MW1000–4000 daltons) at a concentration in the range of 30–50%. The medium is preferably at a pH of about 7.5–7.9. The medium optionally may contain additives such as dimethyl sulfoxide that promote efficient hybridization. The fusion may be carried out using the traditional "tube fusion" technique or by a plate technique in which the parent cells are adhered to the plate by means of a non-toxic binding agent such as peanut agglutinin. The ratio of lymphoblastoid B cells to the immortalizing cell usually will be in the range of about 10:1 to 1:10, more usually about 2:1 to 1:2. A cell ratio of 1:1 is preferred. The parent cells typically will remain in contact with the fusion medium for about 30 seconds to two minutes. Thereafter, the fusion mixture will be diluted by successive or continuous addition of balanced salt solution and then washed with balanced salt solution. After washing, the cells are expanded in an appropriate growth medium and then seeded in microtiter plates containing a suitable selective medium such as enriched hypoxanthine-azaserine medium (Iscove's medium supplemented with 20% fetal calf serum, 14 μg/ml hypoxanthine, and 4 μg/ml azaserine) supplemented with ouabain. After culturing for about 10 to 20 days, unfused parent cells will have died, leaving the hybrids. Desirable hybrids may be subcloned under limiting dilution conditions and single clones may be expanded to produce pure cultures of the desired fusion partner.

The fusion partner may then be tested for resistance to 6-thioguanine and ouabain (if conferred by the parent lymphoblastoid cell line), secretion of less than 40 ng/ml IgM antibodies (by conventional immunoassay techniques such as radioimmunoassay or enzyme immunoassay, e.g., quantitative ELISA), and growth with a doubling rate of about 18 hours.

Selecting cell lines that secrete less than 40 ng/ml IgM antibodies may be accomplished by a number of techniques, including the following: (a) the cell line is cultured (cloned) at a low density, e.g., 0.5 cells/well, (b) the cell line is irradiated with any form of irradiation, including, for example, ultraviolet light or gamma-radiation (e.g., 100–500 R), and the surviving cells are grown in normal medium for, e.g., 10 days, as described by Evans & Vijayalaxmi *Nature* (London) (1981) 292:601–605 (the disclosure of which is incorporated herein by reference), or (c) the cell lines are chemically mutagenized, such as by contacting them with, e.g., ethyl methanesulfonate (e.g., 60–150 μg/ml for 24 hours), and the surviving cells are grown in normal medium for, e.g., 10 days. When any one of these three techniques is used, some or all the clones after a few weeks begin to secrete low levels of endogenous IgM. If the parent cell line is not ouabain resistant, the fusion product may be made to be ouabain resistant, such as by using the technique described by Kozbor et al., *Proc. Natl. Acad. Sci. USA* (1982) 79:6651–6655, the disclosure of which is incorporated herein by reference. Briefly, the cells are seeded in 96-well microtiter plates in the presence of ouabain, cultures are fed every four days with ouabain-containing medium, and wells with viable colonies are scored after two weeks. The surviving cells are subcultured in 24-well tissue culture plates and then grown in flasks in gradually increasing concentrations of ouabain. Dead cells are removed, e.g., by the Ficoll-Isopaque method.

The fusion partner thus obtained may be adapted to growth and maintenance in serum-free medium for large-scale, more reproducible spinner culture production, as described below. Examples of suitable media include HL-1 supplied by Ventrex, Inc. or HB104 supplied by Hana Biologicals.

The fusion partner herein, designated FWIL, may be used as a parental tumor partner in fusions with a variety of other human, animal, or bacterial cells. For making human monoclonal antibody-producing triomas, the fusion partner will be fused to Ig-producing human cells such as, e.g., peripheral blood lymphocytes (PBLs), spleen cells, lymph node cells, bone marrow cells, and synovial tissue cells. Mammalian cells such as murine or rat cells may also be employed, e.g., splenocytes. The antibodies may be of any isotype, including IgG and IgM, with IgG types being specifically exemplified herein. For preparing human antibodies, PBLs are preferred because of their availability. The Ig-producing cells that are fused with the fusion partner herein have been stimulated or sensitized by exposure to a target antigen to produce antibodies against the antigen. The target antigen may be an exogenous antigen or an auto-antigen (i.e., an endogenous material that evokes an autoimmune response). The sensitized lymphocytes may be obtained from patients who have been infected naturally with the target antigen, immunized with the target antigen, or, in the case of autoantigens, from patients who suffer from autoimmune conditions. When in vivo inoculation with the target antigen is involved, the host typically is inoculated with the antigen and given one or more subsequent booster inoculations. Cells are usually collected from the host 2-3 weeks after the final booster.

Alternatively, the cells may be sensitized in vitro by obtaining cells or tissue from the host, preparing a preparation of viable cells, if necessary, and culturing the cells in a nutrient medium that contains the target antigen at an appropriate concentration. When PBLs are used, the nutrient medium also will contain macrophages. The cells typically will be incubated about 2-4 days in the antigen-containing medium.

The fusion protocol described above may be employed for preparing the antibody-producing trioma, wherein the fusogen-containing medium is preferably calcium-free. An alternative is panning, as follows. Cells (PBLs, splenocytes, etc.) are panned on antigen-coated tissue culture plates, then EBV transformed and fused to the fusion partner herein. Panning involves incubation of the population of immunocompetent cells on a plastic surface coated with the relevant antigen. Antigen-specific cells adhere. Following removal of non-adherent cells, a population of cells specifically enriched for the antigen used is obtained. These cells are transformed by EBV and cultured at $10^3$ cells per microtiter well using an irradiated lymphoblastoid feeder cell layer. Supernatants from the resulting lymphoblastoid cells are screened by ELISA against the relevant antigen(s). Cells that are positive for the relevant antigen(s) are expanded and fused to the fusion partner herein. Triomas are selected in ouabain and 6-thioguanine. Supernatants from the selected triomas are tested for IgM or IgG production.

The level of monoclonal antibodies produced by the triomas herein depends on how low is the endogenous IgM secretion of the FWIL fusion partner. IF FWIL is employed that has not been treated by irradiation or chemical mutagenization, the trioma typically produces high titers of IgG monoclonal antibody, usually greater than about 2.5 $\mu$g/ml of spent culture medium. If irradiated or chemically mutagenized FWIL is employed so that the endogenous IgM secretion of the FWIL is very low, typically the IgG monoclonal antibody will be produced in smaller amounts, e.g., about 150 ng/ml.

The triomas that produce the antibodies may be grown in suitable culture medium such as Iscove's media or RPMI-1640 medium (Gibco, Grand Island, N.Y.) or in vivo in immunodeficient laboratory animals. The antibodies may be recovered from the culture medium or body fluid, e.g., ascites fluid or serum of the inoculated host after a suitable inoculation period, as the case may be, by conventional techniques such as, e.g., ammonium sulfate precipitation, ion exchange chromatography, such as diethylaminoethyl (DEAE) cellulose chromatography, affinity chromatography, electrophoresis, microfiltration, and ultracentrifugation.

The types of monoclonal antibodies that may be prepared include those against bacterial infection, such as bacteremia or sepsis, in which the immunogen may be *E. coli* J5 or *S. minnesota* R595 core glycolipids or typhoid. As an alternative example, the immunogen may be tetanus toxin or blood group A, as exemplified in U.S. Pat. No. 4,624,921. The invention herein is not limited to any particular antigen against which the antibodies may be directed. The practitioner will be able to generate the appropriate antibody-producing cell line for fusion with the partner herein.

The dosage regimen and dose of antibody that may be employed in treatment will depend on the antigen against which it is directed, as well as whether the antibody is being administered for therapeutic or prophylactic purposes, the type of patient, and the patient's history. The antibodies may be administered topically, locally, or parenterally, or by continuous infusion. For treatment of bacteremia or sepsis, the total amount of an antibody administered per dose typically will be in the range of about 0.1 to 20 mg/kg of patient body weight, preferably 0.1 to 10 mg/kg of patient body weight.

For parenteral administration, the antibody will be formulated in a unit dosage injectable form (solution, suspension, emulsion) in association with a pharmaceutically acceptable parenteral vehicle. Such vehicles are inherently nontoxic and nontherapeutic. Examples of such vehicles include water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that maintain isotonicity and chemical stability, e.g., buffers and preservatives. The antibody will typically be formulated in such vehicles at a concentration of about 1.0 mg/ml to 100 mg/ml.

In another application, the fusion partner FWIL may be transformed to express a protein by electroporation with a vector, such as a non-transformed plasmid, an EBV-transformed plasmid, or a phage, containing a gene encoding a protein of interest, such as a mammalian protein. The vector must also contain regulatory sequences suitable for expressing the protein in the relevant host cell line such as promoter/operon, leader, initiation and termination sequences, as well as a ribosome-binding site. Examples of suitable proteins to be expressed include lymphokines such as interleukin-2, interferons, and colony-stimulating factors, enzymes, toxins, hormones, antibodies such as IgM or IgG, and tumor necrosis factor.

The method of splicing the appropriate gene and regulatory sequences into a cloning vector is well known in the art of molecular biology. Further, electroporation is well known. Electroporation may be accomplished, for example, by the method described by Potter et al., *Proc. Natl. Acad. Sci.* (USA) 81:7161-7165 (1984), the disclosure of which is incorporated herein by reference. Briefly, the method involves exposing a suspension of cells and cloned DNA to a high-voltage electric discharge. The vector (e.g., plasmid DNA) to be transfected is typically linearized with a restriction enzyme and normally contains a marker for selection of the presence of the vector. The suspension of cells is obtained by centrifuging the actively growing cells in, for example, about $10^6$/ml of medium, suspending in saline without added $Mg^{+2}$ or $Ca^{+2}$, recentrifuging, and resuspending the pellet in saline at a concentration of about $1-2 \times 10^7$ cells per ml. The plasmid vector DNA may be added to the cell suspension in an effective amount, typically about 1-20 $\mu$g/ml. The DNA and cells are then allowed to sit for about five minutes at 0° C. in an electrophoresis chamber, and an electric pulse is applied to the electrodes. After the pulse, the cells and DNA are allowed to sit for, e.g., about 10 minutes at about 0° C. before being added to the growth medium. Cells are grown for about 40–50 hours before transformants are selected in medium supplemented with the appropriate drug to which the vector would confer resistance, e.g., G418 or xanthine, hypoxanthine and mycophenolic acid.

Clones of selected transfected cells are harvested, solubilized, e.g., in guanidine isothiocyanate, and then may be layered on a CsCl cushion. After centrifugation, RNA and DNA may be isolated from the pellet and cushion, respectively. For analysis by Northern or Southern blots, DNA may be digested with a restriction enzyme such as HindIII and electrophoresed in native agarose gels. RNA may be electrophoresed in formaldehyde/agarose gels. After transfer to nitrocellulose, the DNA and RNA may be hybridized with a radioactive probe specific for a marker gene and analyzed by autoradiography. Alternatively, the DNA and RNA can be analyzed by radioimmunoassay using standard techniques.

After analysis the transfected cell line can be grown in sufficient quantity and then induced to express the protein for which the relevant gene codes. Induction conditions will depend on the particular protein and signal sequences.

The various aspects of the invention are described further by the following examples. These examples are not intended to limit the invention in any manner. In the examples, all percentages are by weight if for solids, and by volume if for liquids and all temperatures are in degrees Celsius, unless otherwise noted.

EXAMPLE 1

Antibody Production

Fusion Partners

All cell lines were maintained in Iscove's DME medium (ICM) supplemented with 10% fetal bovine serum (FBS), 2 mM glutamine, and $5 \times 10^{-5}$ M 2-mercaptoethanol. The cell lines were checked routinely for the presence of mycoplasma. For large-scale production of human monoclonal antibodies, the fusion partner FWIL was adapted to serumfree growth in HL-1 medium obtained from Ventrex Labs, Portland, Me., or in HB104 medium obtained from Hana Biologicals, Alameda, Calif.

A. LTR228

LTR228, obtained from the ATCC (HB8502), is a subvariant of the WI-L2 line (Levy, J. A. et al., *Cancer* (1968) 22:517). It was derived from a mycoplasma-contaminated generic WI-L2 parent by cloning the parent in soft agar, decontaminating the parent line, and culturing it in Iscove's medium containing 20 μg/ml 6-thioguanine (6-TG). LTR228 was selected from among the 6-TG resistant clones on the basis of its ability to fuse efficiently with normal B lymphocytes to produce stable human x human hybridomas.

LTR228 has a hyperdiploid modal chromosome number of 8. LTR228 cells are characterized by having: extra copies of chromosome 13 and 20; a Robertsonian translocation between chromosomes 14 and 21; a copy of chromosome 8 with an enlarged short arm composed of a homogeneously staining region; and a marker 21 which has a translocation from the distal end of chromosome 11. LTR228's karyotype is: 48,XY,+13,+20,−14,+t(14q;21q),−21,-+der(21),t(11;21) (q13;p11),pt+. LTR228 secretes small amounts of $IgM_k$ and has a doubling time of about 16 hours. Its rapid growth rate and high cloning efficiency both in soft agar and by limiting dilution are important characteristics of the line.

LTR228 is the subject of U.S. Pat. No. 4,624,921 issued Nov. 25, 1986.

LTR228 cells were made resistant to ouabain by culturing them in ICM containing $10^{-8}$ ouabain. Resistant cells were expanded and the concentration of ouabain was increased gradually. The procedure was repeated until the cells could survive $10^{-6}$ M ouabain. Clones were selected from soft agar supplemented with 6-TG (10 μg/ml) and ouabain ($10^{-6}$ M).

B. U266

U266, obtainable from the ATCC (TIB196), is a human myeloma secreting IgEλ, and was first described by Nilsson et al., *Clin. Exp. Immunol.* (1970) 7:477–489.

Fusion Protocol for LTR228 and U266

The fusion mixture contained PEG 4000, 40% (w/v); dimethylsulfoxide (DMSO), 10% (v/v) in Hank's balanced salt solution (HBSS)−/+($Ca^{2+}$free, 2 mM $MgSO_4$), supplemented with 6 μg/ml poly-L-arginine (Sigma, 70K-150K). Forty grams of PEG 4000 were combined with 10 ml of dimethylsulfoxide (DMSO) and 50 ml of HBSS−/+. The mix was autoclaved for 25 minutes. When the solution had cooled to room temperature, poly-L-arginine from a filter-sterilized 1000x stock solution was added to obtain a final concentration of 5 μg/ml. Before use, the pH of the fusion mixture was adjusted to 7.9 with sterile 0.1 N NaOH. Fresh fusion mixture was made every two to three weeks.

Plates (Costar 3506, 6-well cluster, 35 mm well diameter) were prepared as follows: 2 ml of HBSS−/+and 50 μl of a filter sterilized, 100 μg/ml, peanut agglutinin (PNA, Sigma) were added to each well. Plates were incubated at 37° C. for at least one hour prior to use. PNA stock was stored frozen, and a freshly thawed aliquot was used to coat fusion cells. Smaller sized wells were used if cell numbers were limited.

Parent cells were washed twice in HBSS−/+at room temperature and subsequently resuspended and combined in HBSS−/+warmed to 37° C. Two ml of the suspension (10–20 million cells) were added to each pretreated well containing PNA coating solution. Plates were spun at 400–500 x g, room temperature, for six minutes to form a monolayer of cells. Supernatant was then aspirated off the plates.

Two ml of fusion mixture warmed to 37° C. were carefully added down the side of the fusion cell. After one minute, the PEG solution was diluted with 37° C. 5% DMSO in HBSS−/+(filter sterilized) at a rate of 2 ml/min (0.5 ml every 15 seconds) for three minutes (6 ml). The fusion dilution mixture (FDM) was then added at a rate of 4 ml/min until the well was filled. FDM was always added down the side of the well, so as not to disturb the monolayer, and the plates were constantly swirled to ensure optimal mixing.

At this stage, the wells were aspirated. The remaining film of PEG mixture was diluted at a rate of 2 ml/min for two minutes with warm FDM. Again the plate was constantly swirled. Over a period of 15 seconds, 5 ml of 37° C. HBSS−/+were added to the fusion well, and all supernatant was aspirated from the monolayer. Finally, each fusion well was washed twice with 5–10 ml of warm HBSS−/+. Five ml of warm ICM, 15% FCS, were added to each well, and the plates were incubated at 37° C. The day following fusion the cells were plated at $10^5$ cells/well in ICM containing 6-thioguanine and ouabain ($10^{-6}$ M) Growing cells were fed every four days with ouabain-containing medium, and wells with viable colonies were scored after two weeks. The surviving cells were then subcultured in 24-well tissue culture plates and subsequently grown in flasks in gradually increasing concentrations of ouabain. Dead cells were removed by the Ficoll-Isopaque method. The resulting line was found to be resistant to 6-thioguanine and ouabain. Positive wells were recloned in soft agar and tested for success of fusions. A sample of one of the fusion-positive subclones, designated FWIL, was selected for preservation and deposit.

IgM secretion of FWIL was found to be below 40 ng/ml by a quantitative IgM ELISA as described below.

Adaption to Serum - Free Medium

The FWIL subclone was adapted to growth and maintenance in serum-free medium for large scale production using the following stepwise method:

1. Two days prior to subculturing, the cells were fed with a mixture of Iscove's DME in which they were growing, 50% of the amount of FBS in the medium in which they were growing, and 50% by weight of serum-free medium HL-1 supplied by Ventrex, Inc. or HB104 supplied by Hana Biologicals.

2. Two days later, or when the hybridoma cells reached densitities of $8 \times 10^5$ to $1 \times 10^6$ cells/ml, the cells were subcultured and planted with 60% of Iscove's DME medium and 50% of the serum-free medium. The cells were removed from the latter medium by centrifugation at $200 \times g$ for five minutes. The Iscove's DME medium was mixed with 50% of the serum-free medium to form a 50:50 mixture, in which the cell pellet was suspended and then counted. An appropriate amount of cell suspension was planted in the vessel with 50% Iscove's DME and 50% serum-free medium. The planted cell densities preferably do not fall below $5 \times 10^4$ cells/ml and not exceed $1 \times 10^5$ cells/ml.

3. After two to three days post-planting, or when the cell density reached $8 \times 10^5$ to $1 \times 10^6$ cells/ml, the cells were refed with 50% Iscove's DME and 50% serum-free medium.

4. Step 3 was repeated for another passage.

5. After two to three days in culture or when the cell density reached $8 \times 10^5$ to $1 \times 10^6$ cells/ml and viability was about 85%, the cells were cultured on serum-free medium only. When the cells were planted in the serum-free medium for the first time the cell densities were between $1 \times 10^5$ to $8-9 \times 10^5$ cells/ml.

FWIL was found to grow in HL-1 medium containing L-glutathione, ethanolamine and 2-mercaptoethanol at 5% fetal calf serum but at no smaller concentration.

Selection of Ig-Nonsecreting Clones

1. When the FWIL cells were cloned at 0.5 cells/well, a few nonsecreting clones were obtained which, within 2-3 weeks, began secreting low levels of endogenous IgM.

2. The FWIL cells were mutagen-treated by exposure to UV irradiation at $4 \times 10^6$ cells/ml for 3 minutes. The exposure was carried out in an open 60 mm Petri dish in 2.5 ml per dish (thus, $10^7$ cells). After mutagenic treatment, the cells were allowed a 10-day period of expression in normal medium; survivors were then cloned at one cell/well in 96-well microtiter plates in 0.2-ml volumes. The few surviving nonsecretor cells resumed secretion of a low level of IgM after several weeks.

3. The FWIL cells were mutagen-treated with ethyl methanesulfonate (60–150 $\mu$g/ml) for 24 hours and then the cells were treated as described above for UV irradiation. Many surviving cells were nonsecreting, and some of these, after a few weeks, resumed IgM secretion, but at a still lower level.

Production of Antibodies

1. Fusion Protocol

The fusion mixture contained polyethylene glycol (PEG) 4000, 40% (w/v) and dimethylsulfoxide (DMSO), 10% (v/v), in Hank's balanced salt solution (HBSS)$-/+$($Ca^{2+}$-free, 2 mM $MgSO_4$). Forty g of PEG 4000 was combined with 10 ml of DMSO and 50 ml of HBSS$-/+$. The mix was sterilized by 0.45 $\mu$ filtration. Before use, the pH of the fusion mixture was adjusted to between 7.5 and 8.5 with sterile 0.1 N NaOH. Fusion mix was prepared fresh for each fusion.

Plates (6-well cluster, 35 mm well diameter) were prepared as follows: 1 ml of HBSS$-/+$ and 50 $\mu$l of a filter sterilized, 100 $\mu$g/ml, peanut agglutinin (PNA, Sigma) were added to each well. Plates were incubated at 37° C. for at least one hour prior to use. PNA stock was stored frozen, and a freshly thawed aliquot was used to coat fusion cells. Smaller sized wells were used if cell numbers were limited.

Both parent cell lines were washed twice in HBSS$-/+$ at room temperature and subsequently resuspended and combined at a 1:1 ratio of lymphoblastoid cell line secreting IgG:FWIL in HBSS$-/+$ warmed to 37° C. Two ml of the combined cell suspension (1–2 $\times 10^7$ cells) was added to each pretreated well. Cells were spun onto the bottom of the plate at 400–500 $\times$ g, room temperature, for five minutes to form a monolayer of cells. Supernatant was then aspirated off the plates, leaving behind adherent coating of cells.

Two ml of PEG fusion mixture described above and warmed to 37° C. was carefully added down the side of the fusion cell. After one minute, the PEG solution was diluted with a fusion dilution mixture (FDM) of 5% DMSO (Sigma) in HBSS$-/+$(warmed to 37° C. and filter sterilized) at a rate of 2 ml/min (0.5 every 15 seconds) for the next two-three minutes (4–6 ml). For the next two minutes the FDM was added at a rate of 4 ml/min with mixing. FDM was always added down the side of the well, so as not to disturb the monolayer, and the plates were swirled constantly to ensure optimal mixing.

At the end of the two minutes the wells were aspirated to remove diluted PEG fusion mixture. The remaining film of PEG mixture was diluted at a rate of 2 ml/min for one-two minutes with warm FDM. Again the plate was constantly swirled. Over a period of 0.25-2 minutes with swirling, 5 ml of HBSS$-/+$warmed to 37° C. was added to the fusion well at a rate of 1 ml/15 seconds. The well was then filled up with HBSS$-/+$and all supernatant was aspirated from the monolayer. Finally, each fusion well was washed once or twice with about 5–10 ml of warm HBSS$-/+$, aspirated and washed again with about 5 ml of HBSS$-/+$and aspirated. Five ml of warm Iscove s complete medium and 15–20% FBS, were added to each well, and the plates were incubated at 37° C. for 24 hours. The day following fusion the cells were resuspended at a density of $5 \times 10^5$ cells/ml in Iscove's medium containing 10% fetal calf serum (FCS), azaserine (2 μg/ml), hypoxanthine (100 μM), and ouabain (1 μM) and plated at 51.2 ml/well in 96-well plates. Cultures were subsequently fed every three days. Growing hybrids were visible by day 10–15.

2. Unmutagenized FWIL×IgG Secretor

The FWIL that was not treated with any mutagen was fused with a lymphoblastoid cell line secreting IgG (WGA-23B11), using the fusion protocol described immediately above, to produce the trioma designated IgG Fusion II-29.1 (deposited with the American Type Culture Collection under No. HB9395). The cell line WGA-23B11 is an EBV-transformed IgG secretor obtained from spleen cells from a lymphoma patient. After clean-up with Ficoll, the spleen cells were depleted of suppressor T cells, split into four groups, stimulated with different lectins, including wheat germ agglutinin (WGA) and transformed with EBV. A cell line stimulated with WGA was selected as the best secretor and used to fuse with FWIL.

3. Mutagenized FWIL×IgG Secretor

The FWIL that was irradiated with UV light as described above was fused using the protocol described immediately above with a lymphoblastoid cell line secreting IgG (WGA-23B11 described above), using the fusion protocol described immediately above, to produce the trioma designated IgG Fusion I-2.4 (deposited with the Cetus Type Tissue Collection, Emeryville, Calif., under No. 10,393 on Mar. 25, 1987.

4. Selection/Screening

1. IgM ELISA

Immulon II flat-bottom microtiter plates were coated at 100 μl/well with goat anti-human IgM (Tago) 10 mg/ml in 50 mM bicarbonate buffer (pH 9.6). After 90 minutes at °C, plates were washed with PBS++, 0.05% Tween 20, and preferably 0.01% thimerosal up to five times by immersion or with automated plate washer. Then 100 μl of PBS++, 1% BSA, 0.05% Tween 20, 0.01% thimerosal was added to each well. A total of 100 μl of test supernatant was added to first wells and preferably duplicate two-fold dilutions were made. One well was left as control. The plates were incubated for 30 minutes at room temperature and then washed up to five times as described above. Then, a total of 60–100 μl of peroxidase-conjugated goat anti-human IgM antibody (Tago), diluted in PBS++, BSA, Tween 20 and thimerosal, was added and the mixture incubated for 30 minutes at room temperature and washed five times. Then a total of 200 μl of the ABTS peroxidase substrate described for the bacterial ELISA was added to each well. The mixture was incubated for 30 minutes at 37° C. in the dark and read on an ELISA plate reader ($OD_{405}$) using as IgM standard pooled human myeloma (Cappell) previously standardized versus a Tago Standard.

2. IgG ELISA

This procedure was exactly the same as the IgM ELISA except that analogous anti-human IgG sera from Tago was employed rather than the goat anti-human IgM.

3. Screening

Culture supernatants of both fusions were assayed by IgM and IgG ELISA as described above. Positive wells were subcloned by limiting dilution and reassayed approximately two weeks later. Limiting dilution cloning was performed in 96-well U-bottom plates in Iscove's DME medium with 20% fetal bovine serum.

Twelve triomas from the nonmutagenized trioma and three from the mutagenized trioma were selected based on their titers of exogenous IgM and IgG for expansion. The monoclonal antibodies produced from these triomas were isotyped using the IgM and IgG ELISAs mentioned above. All triomas have been cloned. The nonmutagenized triomas stably produced greater than 2.5 μg/ml IgG and about 1 μg/ml IgM antibody per ml of spent culture media, and the mutagenized triomas stably produced 150 ng/ml IgG and about 1 μg/ml IgM antibody per ml of spent culture media.

Fusion of FWIL or a mutagenized FWIL with human B lymphocytes obtained by vaccinating volunteers with a standard available typhoid injection to produce high LPS antibody titers or obtained from volunteers with naturally acquired high titer serum antibodies to *E. coli* J5 or *S. minnesota* R595, as described in EP Publication No. 174204 published Mar. 12, 1986, is expected to produce monoclonal antibodies that block the adverse biological effects of Gram-negative bacteria endotoxin. The disclosure of the EP publication is incorporated herein by reference. Alternatively, one can use human B lymphocytes from volunteers with cystic fibrosis and serum anti-exotoxin A titers greater than 1:2000 obtained as described in copending U.S. Application Ser. No. 727,514 filed Apr. 26, 1985, the disclosure of which is incorporated herein by reference.

Deposits

All cell lines listed in the table below were deposited at the Cetus Tissue Culture Collection (CTCC), Cetus Corporation, 1450 Fifty Third Street, Emeryville, Calif., USA. Two of them were also deposited at the American Type Culture Collection (ATCC), 12301 Parklawn Drive, Rockville, Md., USA. Deposit dates and accession numbers are given below:

| Cell Line | ATCC Deposit Date | ATCC Accession No. | CTCC Deposit Date | CTCC No. |
| --- | --- | --- | --- | --- |
| FWIL | 2/11/87 | HB9320 | 2/11/87 | 10,350 |
| IgG Fusion II-29.1 | 4/15/87 | HB9395 | 4/15/87 | 10,394 |
| IgG Fusion I-2.4 | | | 3/25/87 | 10,393 |

The deposits above were made pursuant to a contract between the ATCC and the assignee of this patent application, Cetus Corporation. The contract with ATCC provides for permanent availability of the progeny of these cell lines to the public on the issuance of the U.S. patent describing and identifying the deposit or the publications or upon the laying open to the public of any U.S. or foreign patent application, whichever comes first, and for availability of the progeny of these cell lines to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the cell lines on deposit should die or be lost or destroyed when cultivated under suitable conditions, they will be promptly replaced on notification with a viable culture of the same cell line.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are with the scope of this invention. The deposit of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention in addition to those shown and described herein will become apparent to those skilled in the art from the foregoing description and fall within the scope of the appended claims.

What is claimed is:

1. A stable, continuous human cell line comprising a human immortalizing cell fused to an Epstein-Barr-virus-transformed human lymphoblastoid B cell line wherein the immortalizing cell is myeloma U266 cell line or is derived from said cell line, and the lymphoblastoid B cell line is LTR228 cell line, said stable cell line being characterized by its resistance to 6-thioguanine and ouabain, its secretion of less than 40 ng/ml of IgM antibodies, and its growth with a doubling time of about 18 hours, or progeny of said cell line.

2. The cell line of claim 1 that is further characterized by being adapted to serum-free medium.

3. The cell line of claim 2 designated FWIL having ATCC No. HB9320 or a cell line derived therefrom.

4. A monoclonal antibody-producing human-$\times$human$\times$human trioma of:
   (a) a stable, continuous human cell line comprising a human immortalizing cell fused to an Opstein-Barr-virus-transformed human lymphoblastoid B cell line, said stable cell line being characterized by its resistance to 6-thioguanine and ouabain, its secretion of less than 40 ng/ml of IgM antibodies, and its growth with a doubling time of about 18 hours, or progeny of said cell line;
   (b) an antibody-producing human cell; wherein
   (c) the antibody-producing human cell is a lymphoblastoid cell line secreting IgG and the human cell line is FWIL having ATCC No. HB9320.

5. A method for producing cell line ATCC HB9320 comprising:
   (a) fusing human immortalizing cells with an Epstein-Barr-virus-transformed human lymphoblastoid B cell line wherein the immortalizing cell is the myeloma U266 cell line or is derived from said cell line and the lymphoblastoid B cell line is BTR 228 cell line, in a fusion medium containing a fusogen;
   (b) separating the cells from the fusion medium;
   (c) incubating the cells in a nutrient for a sufficient time to expand the number of viable cells;
   (d) growing the expanded cells in a medium and selecting those cells that are 6-thioguanine and ouabain resistant; and
   (e) selecting the cell line for secretion of less than 40 ng/ml of IgM antibodies.

* * * * *